United States Patent
Cardarelli

[11] Patent Number: 6,099,309
[45] Date of Patent: Aug. 8, 2000

[54] DISPOSABLE PROPHY ANGLE

[76] Inventor: Venanzio Cardarelli, 20 N. Triangle Dr., Plymouth, Mass. 02360

[21] Appl. No.: 09/431,914

[22] Filed: Nov. 2, 1999

[51] Int. Cl.[7] .................................................. A61C 3/06
[52] U.S. Cl. ............................................ 433/125; 433/166
[58] Field of Search ............................ 433/82, 125, 126, 433/166

[56] References Cited

U.S. PATENT DOCUMENTS

| | | | |
|---|---|---|---|
| 1,907,286 | 2/1933 | Chott | 433/166 X |
| 2,656,559 | 10/1953 | Wiseman | 433/166 X |
| 3,939,599 | 2/1976 | Henry et al. | 433/125 X |
| 4,266,933 | 5/1981 | Warden et al. | 433/125 X |
| 4,544,356 | 10/1985 | Gardella et al. . | |
| 5,040,978 | 8/1991 | Falcon et al. . | |
| 5,083,922 | 1/1992 | Yale | 433/166 |
| 5,219,285 | 6/1993 | Meller et al. . | |
| 5,433,605 | 7/1995 | Strobl, Jr. . | |

*Primary Examiner*—Nicholas D. Lucchesi
*Attorney, Agent, or Firm*—D. Michael Burns

[57] ABSTRACT

A disposable right angle dental handpiece comprising a plastic housing having a sleeve, a tapered neck, a head and a disposable prophy cup. The cup being removably coupled to a driven rotating member located in the head section for simultaneously cleansing the surface of the teeth as well as the surrounding tissue and gingival crevice. The sleeve having an elongated opening for receiving a power drive from a dental unit. A gear ratio mechanism located in the sleeve, rather than in the head section, for increasing the shaft speed by a factor of two to three times. A gear to gear arrangement in the head section for transferring the directional rotation from the drive shaft to the prophy cup. The prophy cup comprising a flexible body having a cavity therein with a plurality of concentric rings made of cloth or felt material for holding the cleansing paste and also to avoid splattering.

17 Claims, 3 Drawing Sheets

DISPOSABLE PROPHY ANGLE

BACKGROUND OF THE INVENTION

1. Field of the Invention

The present invention relates generally to a dental prophylaxis angle (prophy angle), and in particular to a disposable prophy angle having a disposable prophy cup.

2. Description of the Prior Art

It is well known in the prior art to use disposable prophy angles having disposable prophy cups for performing dental procedures by a dentist or hygienist. These prophy angles are driven by a motorized dental handpiece. They are usually connected to the handpiece by inserting a nose section of the handpiece into the angle and connecting it to a drive shaft of the angle. The primary purpose of using a prophy angle is to enable the hygienist to reach more easily the various surface areas of the teeth. The main obstacles in this procedure are the hygienists hands, visibility, access and the size of the angle itself.

The prophy cups are shaped to hold a desired amount of abrasive medium (paste) which is used to clean and polish the teeth. The prior art teaches of ways to automatically feed the paste or, in other cases, to preload a definitive amount of paste. Upon performing the procedure, the prophy cup and angle are subject to contamination and infection from saliva and blood of the patient. The high cost of sterilizing these items, in terms of money and time, has made the use of reasonably priced disposable angles very practical. Another advantage in using disposable mechanisms is to eliminate the need for the dentist or hygienist having to actually handle the components during sterilization. But most importantly, is to reduce the danger from incomplete sterilization, whereby the bacteria and infection are then transferred from one patient to another.

Since every hygienist can consume thousands of disposable prophy angles each year, it is very important that they be reasonably priced. Most of the disposable prophy angles are manufactured from plastic material or inexpensive metals. Usually the plastic materials are of different grades and types depending on whether the component parts are designed to be gears, shafts or housings. Although they are used but a single time, the prior art recognizes the need for ruggedness and durability in disposable angles. It is also imperative that they not break or splinter during use.

As stated above, the primary purpose of the prophy angle is to more easily reach the various surfaces of the teeth. Unfortunately the designs of the prior art locate the main gear reduction in the head section of the prophy angle. This creates a bulkiness where it is least desired. This also demands that the housing leading to the head be larger than necessary. It also makes the weight of the prophy angle heavier at the distal end causing a balancing problem. These designs limit the length of the housing and therefore bring the hygienists hands closer to the mouth of the patient. This causes the patient to experience more discomfort, creates a visibility problem and leads to fatique of the hygienist's hands.

It is well known in the prior art that "splatter" is a problem that happens when the paste is not handled correctly by the prophy cup. There are numerous patents which address this problem. Some seek a solution in the design of the cup, while others attempt to solve the problem by providing a shield or some similar type barrier. The present invention seeks to improve upon the prior art.

Accordingly, a need will be seen for a prophy angle which will alleviate these problems and accomplish the desired end result. A discussion of the prior art, of which the present inventor is aware, and the distinctions from the present invention is provided below.

U.S. Pat. No. 5,433,605 issued to Strobl, Jr. on Jul. 18, 1995, discloses an adjustable prophy angle of which the angle can be adjusted from the standard 90° to improve accessibility. The bulkiness of the angle appears to remain, if not worse, and the visibilty is not seen to be improved.

U.S. Pat. No. 5,219,285 issued to Meller et al. on Jun. 15, 1993, discloses a disposable right angle which utilizes a three piece construction with one of the pieces being made of metal to increase durability. The metal component is insertable through the housing which increases the bulkiness of the angle.

U.S. Pat. No. 5,040,978 issued to Falcon et al. on Aug. 20, 1991 shows a dental prophy angle having a single snap-on retention mechanism that is integral with the housing for retaining the prophy cup rotating member and providing smooth rotation of the cup. This is an excellent illustration of the prior art and the effort that has been made to make the angles easy to assemble. Although this feature is of importance, it does not make the access any easier nor reduce the visibility problem.

U.S. Pat. No. 4,544,356 issued to Gardella et al. on Oct. 1, 1985 teaches the use of a main shaft and a secondary shaft, but rather than utilizing a gear mechanism this patent uses a reciprocating cam to impact a reciprocating action to the cup. No attempt is made here for any gear reduction.

None of the above inventions and patents, either singly or in combination, is seen to describe the instant invention as claimed.

SUMMARY OF THE INVENTION

Accordingly, the above problems and difficulties are obviated by the present invention which provides for a disposable prophy angle to be used in association with motorized dental handpieces.

More particularly, the present invention is comprised of four major sections, a sleeve, a neck, a head and a prophy cup attachment. The main inventive concept of the present invention being the utilization of a gear ratio system at a relative distance from the head. This gear ratio taking place in the sleeve section, which has the largest cross sectional area. A secondary shaft, leading from the location of the gear ratio, needs to be only a fraction of the size of the main drive shaft. This allows the neck section to be thinner, thereby allowing greater visibility for the hygienist. Also, by having the gear ratio take place in the sleeve section, the heaviest portion of the prophy angle is in the handle. This will create a more balanced prophy angle, one that will be easier for the hygienist to control, cause less fatigue, give better access, and it will also help to keep the hands of the hygienist out of and away from the patients's mouth.

The working member of the prophy angle is a prophy cup which is different than the prior art, in that it will have a plurality of concentric rings disposed within the inner cup, which will help eliminate splatter. These rings will have varying levels of abrasivity; the most abrasive being at the deepest portion of the cup. The rings being made of materials such as cloth or felt. As an option, the inner core of the cup may have a multitude of relatively short bristles for increased abrasion. The density and type of material of the bristles a function of the abrasivity. The gearing in the head section will have a greater surface area of contact. Since the gear ratio has already been performed in the sleeve section, the cup will exhibit less wobbling and less vibration, because the central axis of the head end will be shorter in length than comparable devices. Indirectly this also will have an effect in the reduction of splatter. The part of the prophy cup that is in contact with the tooth surface is a molded rubber. During the dental procedure it is often desired and necessary to change the cup texture. The types of rubber used to make the cups can range from relatively soft to sandpaper hard. It is also appreciated that in lieu of the hygienist changing cups, that they can be factory installed with ratings such as soft, medium and hard.

An important object of the present invention is to provide a prophy angle that is inexpensive to manufacture and that is totally disposable.

Another object of the present invention is to provide a prophy angle that will have greater access to tooth surface as well as gingival tissue.

Still another object of the present invention is to provide a gear ratio closer to the hands for greater balance, thereby causing less fatigue and stress to the hands of the hygienist. The major benefit, in providing this gear reduction, is that less air is required to drive the system. Beyond any economical considerations, less air means less vibration and increased frequency of rotation at the head end of the cup, thereby less movement of the cup. This will allow the cup to glide over the teeth more easily, thereby causing more effective surface polishing and better elimination of plaque.

An object of the present invention is to make a prophy angle that will give the hygienist greater range of visibility during the procedure and also reduce vibration to the hands.

Another object of the invention is to impart to the prophy angle a true spin concentricity which will minimize wobble and thereby reduce splatter from the paste medium.

A further object of the invention is to provide a prophy cup that will have varying levels of abrasion created by a plurality of concentric rings made from cloth or felt materials.

Still another object of the invention is to provide a prophy cup that will have an inner core made from varying densities of nylon bristles.

These and other objects of the present invention will become readily apparent upon further review of the following specification and drawings.

DETAILED DESCRIPTION OF THE PREFERRED EMBODIMENT

Figure 1:
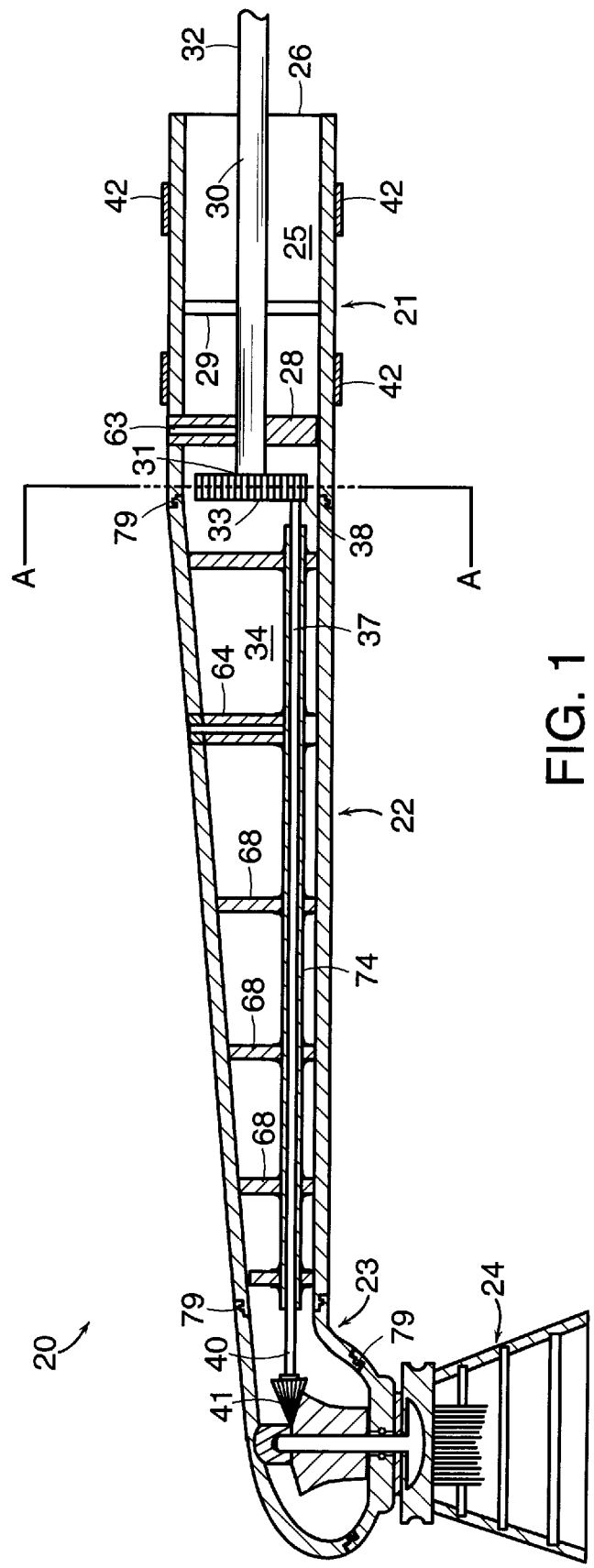
FIG. 1 is a longitudinal sectional view showing the disposable prophy angle with prophy cup mounted therein.

Referring now to the drawings, and in particular to FIG. 1, reference numeral 20 indicates a disposable dental prophylaxis (prophy) angle of the present invention. The angle 20 includes a sleeve section 21, a tapered neck section 22, a head section 23 and a prophy cup 24. Sleeve section 21, having means 79 for snap-fitting into neck section 22 and neck section 22 having similar means 79 for snap-fitting into the head section 23. The lower head section 23 also having means 79 for opening and closing head section 23. Conventional means for connecting the sections are well known in the art. These connections can also be made by bonding the mating surfaces by suitable adhesives, sonic welding or other known techniques.

Figure 2:
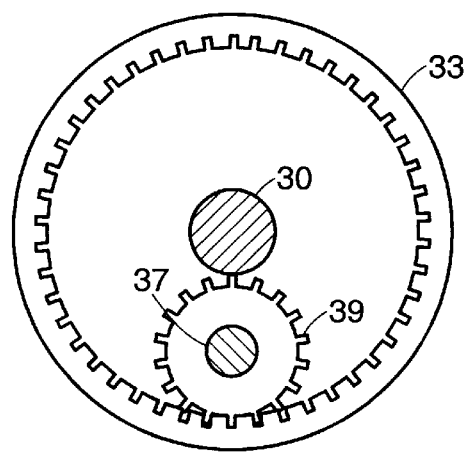
FIG. 2 is a front elevational view of the main and secondary gears taken on lines A—A of FIG. 1.

Sleeve section 21 is comprised of a thin outer shell made from a disposable plastic material, a plastic that is FDA approved such as a polycarbonate resin like that marketed under the General Electric trademark LEXAN. Sleeve section 21 has a generally cylindrical elongated passageway 25 therein, and an opening 26 of sufficient diameter to accept the nose portion of a conventional dental handpiece (not shown). The handpiece is usually air or electrically driven and connected to a dental unit. Located in close proximity to opening 26 is a standard "T" shaped keyslot (not shown) for securing the dental handpiece in place. It is presumed that this mounting means can be adapted to accept a variety of handpieces, without deviating from the intent of the present invention. Integrally interposed within passageway 25 are support struts 28. Struts 28 provide stability to sleeve 21, thereby eliminating the need for a thicker shell. Each strut 28 will have an orifice 63 leading to a conduit 64, for allowing the hygienist to periodically add dental oil for lubrication. This will be important on units designed to be permanent and thereby autoclaved, however even on disposable angles 20 it may be desired to decrease friction from time to time. An integrally interposed 360° stop 29 is positioned to orient the dental handpiece and insure that it will be properly inserted within sleeve section 21. Transversing longitudinally through passageway 25 is a main drive shaft 30, which has a proximal end 31 and a distal end 32. Proximal end 31 having a main drive gear 33 integrally connected to it. As shown in FIG. 2, drive gear 33 has internal teeth. Distal end 32 of drive shaft 30 connects with the drive input of the dental handpiece. Struts 28 and stop 29 both provide support, stabilization and alignment for drive shaft 30. Struts 28 and stop 29 being molded from the same type of plastic as sleeve section 21. Drive shaft 30 and drive gear 33 are generally made from a different grade of plastic. Gears usually require more flexibility and therefore a plastic such as an acetal copolymer available under the Celanese trademark CELCON as well as many others can be used. The exterior surface of sleeve section 21 can have rubber soft pads 42 dispersed to help reduce vibration to the hands of the hygienist. These pads 42 can be manufactured as part of the prophy angle 20 or else can be removably placed on sleeve section 21.

Figure 3:
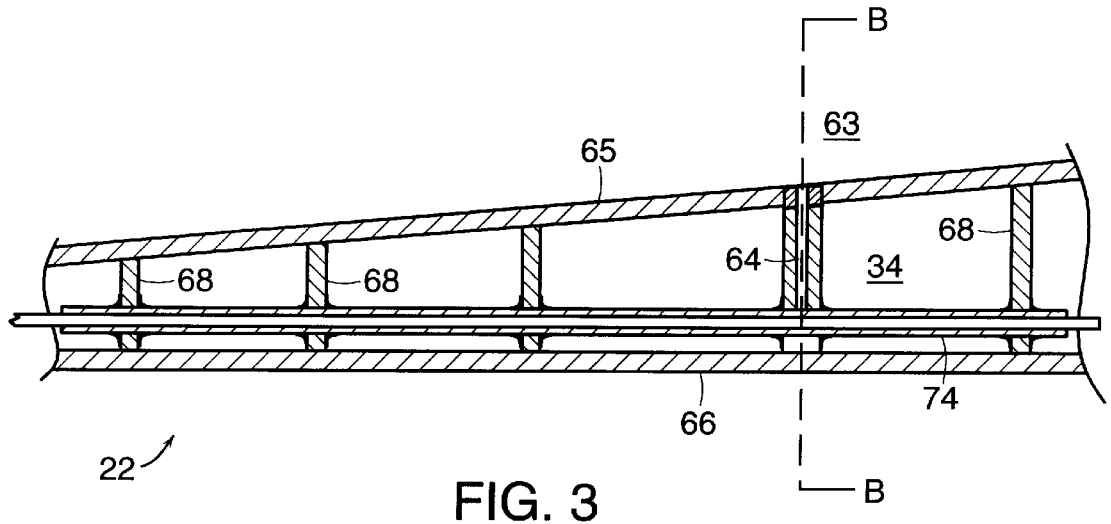
FIG. 3 is a longitudinal cross sectional view of the neck section.
Figure 4:
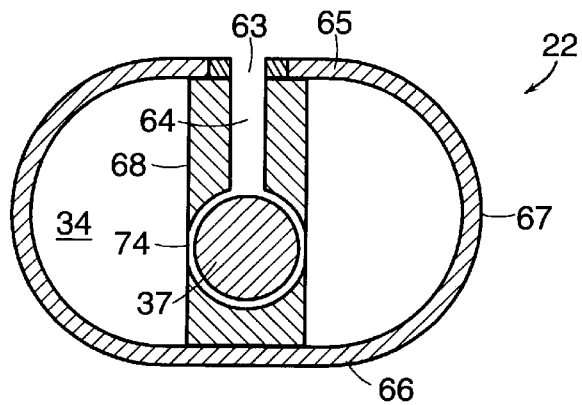
FIG. 4 is a cross sectional view of the neck section taken on lines B—B of FIG. 3.

As depicted in FIGS. 3 and 4, neck section 22 is elongated 20 and tapered (quite significantly in respect to other conventional prophy angles) and has a cross sectional shape that is flat on the top and bottom surfaces 65 and 66 while having elliptical side surfaces 67. Neck section 22 is made from the same plastic as sleeve section 21. The elongated tapering shape allows the hygienist to have greater visibility and also increases the comfort level of the patient. The interior of neck section 22 is a hollow chamber 34. Interposed within chamber 34 are neck struts 68 which are integral with neck section 22 and in addition to supporting neck section 22 also provide support for an optional stability tube 74 that will further eliminate vibration in the system. Neck struts 68 have a shape mirroring the hollow chamber 34. Stability tube 74 passes longitudinally through the chamber 34 and provides the support and alignment of a secondary shaft 37. Shaft 37 moves longitudinally through tube 74 and has a first end 38 integrally connected to a secondary gear 39. Secondary gear 39 having externally mounted teeth for meshing with drive gear 33, as shown in FIGS. 1 and 2, whereby secondary shaft 37 will have the same rotational direction as main drive shaft 33. A main inventive concept of the present invention is in providing this gear ratio away from head section 23. Second end 40 of secondary shaft 37 having a spirally shaped driving gear 41 extending from the neck 22. Spiral driving gear 41 having teeth that gradually narrow from the outer extremity to the inner core. The advantages of this will be stated later. Neck section 22 having orifices 63 for introducing oil which is a necessity for reusable prophy angles. The oil flows through conduits 64 for lubricating secondary shaft 37. It is to be appreciated that the slim and elongated shape of neck section 22, and the distribution of the gearing ratio to sleeve section 21, allows for a more balanced angle 20 with the weight closer to the hygienist's hands. This will help to reduce stress and fatigue.

Figure 5:
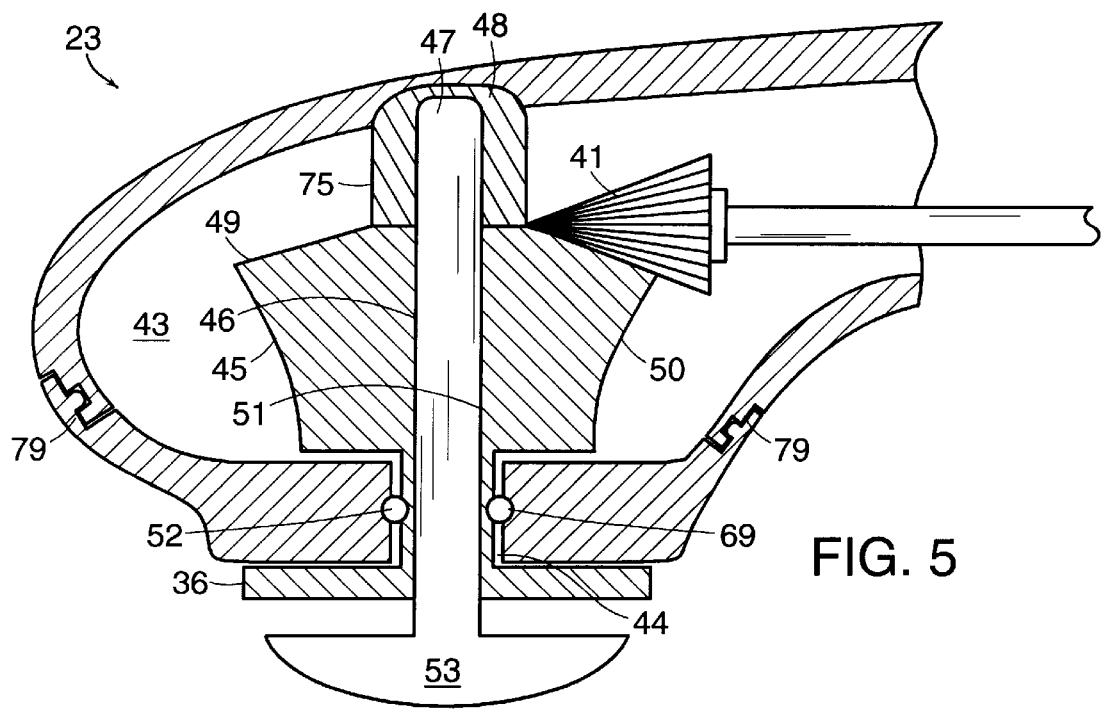
FIG. 5 is a cross sectional view of the head section and the relationship of the driving and driven gears.

Head section 23 and its relationship to neck section 22 and prophy cup 24 are best described by FIG. 5. Head section 23 is made from the same disposable plastic as sleeve section 21. It is critical for the exterior surface of the head 23 to be extremely smooth so as to eliminate possible irritations with 5 the inner membranes of the mouth and tongue. The design of the present invention enhances this concept as rounded head section 23 and neck section 22 are not only smooth but smaller than conventional disposable prophy angles. Within head section 23 is a cavity 43. The bottom of head section 23 having a snap fitting means 79 to allow access. An opening 44 is defined in the lower portion of head section 23. A rotating mandrel 45 is seated within cavity 43. Mandrel 45 having a central axis pole 46 integrally fixed to it, with axis pole 46 extending both upwardly and downwardly from mandrel 45. The top part 47 of axis pole 46 is rotatively positioned within a recess 48 in the inner shell of head 23. Insuring proper alignment and spatial positioning of mandrel 45 is a hollow cylindrical sheath 75 that extends downwardly to the upper portion of mandrel 45, which has a spirally shaped bevel driven gear 49 therein. Gear 49 is put into direct engagement with the spirally shaped driving gear 41 of secondary shaft 37. The result being a greater contact surface between gear teeth 41, 49. The greater gear surface area means a reduction in weight, more spin and less energy expenditure. Driving gear 41 approaches driven gear 49 at a right angle but maintains a 3600 groove, whereby gears 41, 49 are locked throughout the rotation. Mandrel 45 has a cup-like shape with tapering concentric sides 50. The bottom surface 35 of mandrel 45 is integrally connected to a circular boss 36 by a concentric slot 69. Slot 69 maintains boss 36 in a generally parallel spatial relationship to bottom surface 35. Mandrel 45 is located in head section 23 maintaining proper position within head 23 by boss 36 and concentric slot 69. Boss 36 having a diameter larger than cup opening 44 and thereby forming a seal with cup opening 44. Slot 69 having a friction fit with the perimeter of cup opening 44. At the bottom of axis pole 46 is an integrally connected receiving button 53 which has a rounded shape and designed for mounting of a disposable prophy cup 24. Heat caused by friction, when combined with vibration, is a major factor of increased splattering. The present invention is designed to eliminate harmful vibration. An improved design incorporates a circular channel 51 defined within concentric slot 69. A plurality of ball bearings 52 are dispersed within slot 69 in frictionless contact with central axis pole 46.

Figure 6:
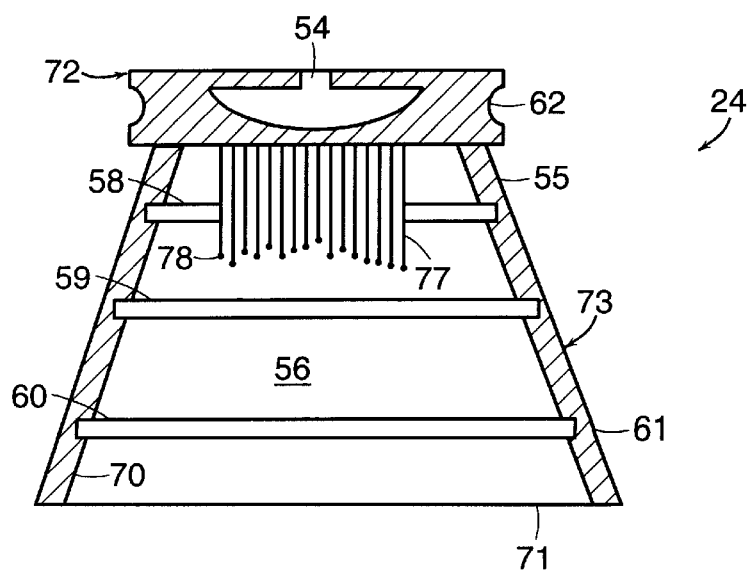
FIG. 6 is an elevational cross sectional view of a symmetrical prophy cup.

FIG. 1 illustrates the relationship of prophy cup 24 to head section 23 with particular emphasis on the mounting of cup 24 to receiving button 53. As shown in FIG. 6, the top side of cup 24 has an adapter portion 72 containing a rounded aperture 54 therein for friction fitting over the button 53. Cup 24 having a conically shaped portion 73 with an exterior concentric surface 55. The inner surface 70 of the conically shaped portion having a bore 56. The inner surface 70 having defined therein a plurality of concentric rings. The rings increasing in abrasivity as they are disposed closer to the inner core of cup 24. The preferred embodiment depicts three such rings, an inner ring 58 of greatest abrasivity, a middle ring 59 of lesser abrasivity, and an outer ring 60 having the least amount of abrasivity. The materials for the rings are selected from various cloth and felt materials. The manner in which they are implanted into cup 24 is by conventional methods such as adhesives or heat treating. At the inner core of cup 24 are a multitude of nylon bristles 77, each having tips 78 at their distal ends. Tips 78 being made of nylon or felt material. The densities in which bristles 77 are dispersed is a direct function of the desired abrasiveness of cup 24.

The concentricities allow the hygienist to maneuver the working part of cup 24 into and over areas that would be very difficult to cover without concentricities 58–60. A major benefit of the concentric ring design is in reducing, if not totally eliminating "splattering". Splattering is caused by the non-true torque of cup 24 combined with cup design and the ability or inability of cup 24 to hold the paste. Often at high speeds cup 24 has a tendency to wobble. The gear reduction being performed away head section 23 plus the large surface area of contact between driving gear 41 and driven gear 49 also tends to reduce the wobbling effect. Exterior cup surface 55 having a portion nearest bore opening 71 which has a scored surface 61 for better abrasive qualities between prophy cup 24 and the gingival tissue. The abrasivity of scored surface 61 being varied depending upon the tenaciousness of the plaque. Encircling about adapter portion 72 and cup 24 is a circumferential groove 62 for application of a removal tool which may be available but not herein disclosed. Prophy cup 24 is made of a molded rubber such as butyl rubber, but it is acknowledged that there are many excellent molded rubbers that can be used. The texture of cup 24 will vary during the procedure. It is anticipated that cup 24 can be augmented by impregnations around the outer perimeter with cloth, felt or sponge materials that are sometimes beneficial in removing tenacious plaque and stains.

In cleaning a patient's teeth and gums, a hygienist applies a cleaning compound to the surface of the prophy cup and then applies the rotating prophy cup 24 to the patient's teeth. It is most important that the hygienist have the best vision possible, as working in the confines of a patient's mouth is already a difficult task. The preferred embodiment of the disposable prophy angle 20 and the prophy cup 24 described above, provides a distinct advance in the field of prophylaxis procedures. It provides a means for positioning the main gearing away from the head of the angle, thus reducing the size and weight of head end 23. By using the present invention's secondary shaft arrangement, the neck section 22 can be substantially reduced. Both of these improvements aid the visibiltiy and balance of the angle 20.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

LEGEND

20 Prophy angle
21 Sleeve section
22 Neck section
23 Head section
24 Prophy cup
25 Passageway in sleeve section
26 Opening in passageway for contra-angle
28 Support strut
29 360° Stop
30 Main drive shaft
31 Proximal end of main drive shaft
32 Distal end of main drive shaft
33 Main drive gear
34 Hollow chamber in neck section
35 Bottom Surface
36 Circular Boss
37 Secondary shaft
38 First end of secondary shaft
39 Secondary gear
40 Second end of secondary shaft
41 Spiral driving gear
42 Rubber pads on outer surface of neck section
43 Cavity inside head section
44 Cup opening
45 Mandrel
46 Central axis pole
47 Top portion of central axis pole
48 Recess
49 Driven gear on top surface of mandrel
50 Tapered concentric side surface of mandrel
51 Circular Channel
52 Ball bearings
53 Receiving button
54 Circular aperture
55 Outer concentric surface of conical cup
56 Bore within the conical cup
58 Inner concentric ring
59 Middle concentric ring
60 Outer concentric ring
61 Scored surface of 55
62 Circumferential groove
63 Orifice
64 Conduit
65 Top flat surface of neck section
66 Bottom flat surface of neck section
67 Elliptical side surfaces of neck section
68 Neck struts
69 Concentric Slot
70 Inner surface of conical cup
71 Bore opening
72 Adapter portion of prophy cup
73 Conically shaped portion of prophy cup
74 Stabilizer tube
75 Cylindrical sheath
77 Nylon bristles
78 Bristle tips
79 Means for snap-fitting sections together

I claim:

1. A disposable prophy angle comprising:
   (a) an elongated sleeve section, the sleeve section comprising:
      (i) a longitudinal passageway therein,
      (ii) one end of the sleeve section defining an opening having a diameter of sufficient size for allowing penetration by a motorized dental handpiece being connected to an electrical or air power source,
      (iii) a main drive shaft cointensively transversing through the passageway having a proximal end and a distal end having means for connecting to the main power source,
      (iv) a main drive gear integrally connected to the proximal end of the main shaft;
   (b) an elongated tapered neck section having one end connected to the other end of the sleeve section, the neck section comprising:
      (i) a lower flat surface, an upper flat surface, and elliptical side surfaces defining a hollow chamber extending the length of the neck section therein,
      (ii) a secondary shaft transversing through the chamber, the secondary shaft having a first end and a second end,
      (iii) means for supporting the secondary shaft within the chamber,
      (iv) a secondary gear integrally connected to the first end of the secondary shaft having externally extending teeth for meshing with the main gear whereby the secondary shaft will have the same rotational direction as the main drive shaft,
      (v) a spirally shaped driving gear integrally fixed to the second end of the secondary shaft;
   (c) a rounded head section having an end connected to the other end of the neck section, the head section comprising:
      (i) a cavity included therein,
      (ii) means for latching open and shut the bottom portion of the head section,
      (iii) the bottom portion of the head section having a cup opening,
      (iv) the cavity having a recess defined therein,
      (v) a rotating mandrel disposed within the cavity having a central axis pole extending outwardly from the top and bottom surface of the mandrel, the bottom surface in parallel relationship with the rounded head section,
      (vi) the top portion of the axis pole rotatively received within the recess,
      (vii) a cylindrical sheath extending downwardly from the recess for providing support, stabilization and alignment of the mandrel
      (viii) a receiving button integral with the bottom portion of the central axis pole,
      (ix) means for locking the mandrel in position within the cavity,
      (x) a beveled driven gear integrally mounted on the upper surface of the mandrel and being in a right angle relationship to the driving gear whereby the receiving button is rotatively put into motion; and
   (d) a prophy cup removably mounted on the receiving button.

2. The disposable prophy angle of claim 1, wherein the sleeve section comprises at least one circular strut being interposed in a perpendicular direction to the passageway, for providing stability for the sleeve section and proper alignment as well as support for the main drive shaft.

3. The disposable prophy angle according to claim 2, wherein the sleeve section comprises a circular stop for correctly positioning the leading nose of the motorized handpiece within the passageway, for stabilizing the sleeve section and adding support for the main drive shaft.

4. The disposable prophy angle according to claim 3, wherein the secondary support means comprises a plurality of neck struts being in a perpendicular direction to the chamber, an elongated stability tube extending through the neck struts for housing the secondary shaft in a rotational fit.

5. The disposable prophy angle according to claim 4, wherein each of the struts sections include:

an orifice in the outer surface; and a conduit extending from the orifice to the shaft supported by the strut, whereby the hygienst can add a dental oil for lubrication of the rotating shaft.

6. The disposable prophy angle according to claim 5, wherein the sleeve section includes rubber pads dispersed upon the outer surface for providing a reduction of vibration to the hands of the hygienist or dentist.

7. The disposable prophy angle according to claim 6, wherein the mandrel deposed within the head section has a downwardly and concentrically tapering exterior surface.

8. The disposable prophy angle according to claim 7, wherein the mandrel locking means comprises:

a generally circular boss positioned outside of a lower surface of the head; and a concentric slot integrally connecting in spatial and parallel relationship the boss and the bottom surface of the mandrel, whereby the boss forms a seal and lock against inadvertent drifting of the driven gear when in full engagement with the driving gear.

9. The disposable prophy angle according to claim 8, wherein the concentic slot comprises:

a concentric channel defined in the inner surface of the slot; and a plurality of ball bearings disposed within the channel for allowing frictionless spin to the axis pole, whereby the button will rotate with a minimum of wobble or vibration.

10. A disposable prophy angle according to claim 9, wherein the prophy cup includes:

a rounded adapter portion and a conically shaped outer cup portion;

the adapter portion having a circular aperture therein for slipping over the receiving button;

the cup portion having a bore within the cup surface; and a plurality of concentric rings of varying degrees of abrasivity disposed within the bore of the cup, the rings imparting to the rotating cup true spin rotation while holding a paste medium, whereby there is a virtual elimination of splattering during the prophylaxis procedure.

11. A disposable prophy angle according to claim 10, wherein the prophy cup includes a scoring on the exterior surface of the cup for increased abrasivity between cup and tooth surfaces.

12. The disposable prophy angle according to claim 11, wherein the prophy cup includes a circumferential groove deposed around the adapter portion, the groove being adaptable for gripping by a removal tool.

13. A disposable prophy cup for mounting to a dental prophy angle, the prophy cup including:

a generally rounded adapter portion having a rounded aperture for slipping over the receiving means of the angle;

a conically shaped cup portion having a bore therein;

a circumferential groove about the adapter portion for gripping by a removal tool;

a plurality of concentric rings of varying levels of abrasivity disposed within the bore of the cup for holding a cleaning and abrasion medium, the rings eliminating splattering during the prophylaxis procedure;

the exterior surface of the cup portion being scored to increase the abrasivity between the cup and the surfaces of the gingival tissue; and a multitude of nylon bristles having tips, the bristles dispersed about the center care of the cup for increased abrasion.

14. The disposable prophy cup according to claim 13, wherein the tips of the bristles are made of nylon material.

15. The disposable prophy cup according to claim 14, wherein the tips of the bristles are made of felt material.

16. The disposable prophy cup according to claim 13, wherein the concentric rings are made of cloth material.

17. The disposable prophy cup according to claim 13, wherein the concentric rings are made of felt material.

* * * * *